(12) United States Patent
De Kock et al.

(10) Patent No.: US 7,016,033 B2
(45) Date of Patent: Mar. 21, 2006

(54) COUNTING CHAMBER PROVIDED WITH A REFERENCE AND METHOD FOR MANUFACTURING A COUNTING CHAMBER PROVIDED WITH A REFERENCE

(75) Inventors: Alfons Petrus Antonius Gerrit De Kock, Wilnis (NL); Joannes Hendricus Wilhelmus Cornelis Van Stralen, Heerhugowaard (NL); Hendrik Jan Westendorp, Uithoorn (NL); Corne Arjen Westerveld, Niedorp (NL)

(73) Assignee: Cellvision Technologies B.V.I.O., Heerhugowaard (NL)

( * ) Notice: Subject to any disclaimer, the term of this patent is extended or adjusted under 35 U.S.C. 154(b) by 324 days.

(21) Appl. No.: 10/182,367

(22) PCT Filed: Jan. 25, 2001

(86) PCT No.: PCT/NL01/00050

§ 371 (c)(1),
(2), (4) Date: Nov. 15, 2002

(87) PCT Pub. No.: WO01/55768

PCT Pub. Date: Aug. 2, 2001

(65) Prior Publication Data

US 2003/0107731 A1    Jun. 12, 2003

(30) Foreign Application Priority Data

Jan. 28, 2000   (NL) .................................... 1014217

(51) Int. Cl.
*G01N 1/10*   (2006.01)
(52) U.S. Cl. ...................... 356/246; 356/440; 422/100
(58) Field of Classification Search ............... 356/335, 356/244, 246, 440; 436/527; 422/100, 101; 359/396, 397, 398; 435/284.1, 289.1, 294.1, 435/297.4, 304.1, 304.2, 305.1, 305.2, 305.3, 435/305.4, 305.5
See application file for complete search history.

(56) References Cited

U.S. PATENT DOCUMENTS

| 3,146,103 A | | 8/1964 | Rooney |
| 4,441,793 A | * | 4/1984 | Elkins ........................ 359/398 |
| 6,143,496 A | * | 11/2000 | Brown et al. .................. 435/6 |

FOREIGN PATENT DOCUMENTS

| DE | 44 03 308 A1 | 8/1995 |
| JP | 58211658 | 12/1983 |
| WO | WO 99/00689 | 1/1999 |

* cited by examiner

Primary Examiner—Hwa (Andrew) Lee
Assistant Examiner—Roy M. Punnoose
(74) Attorney, Agent, or Firm—The Webb Law Firm

(57) ABSTRACT

Disclosed is a counting chamber for optical detection of particles that are present in a fluid, comprising two substantially transparent and substantially parallel plates of material, between which the fluid can be introduced. At least one of the plates includes a visible reference, which comprises a relief formed on the surface of the plate.

16 Claims, 1 Drawing Sheet

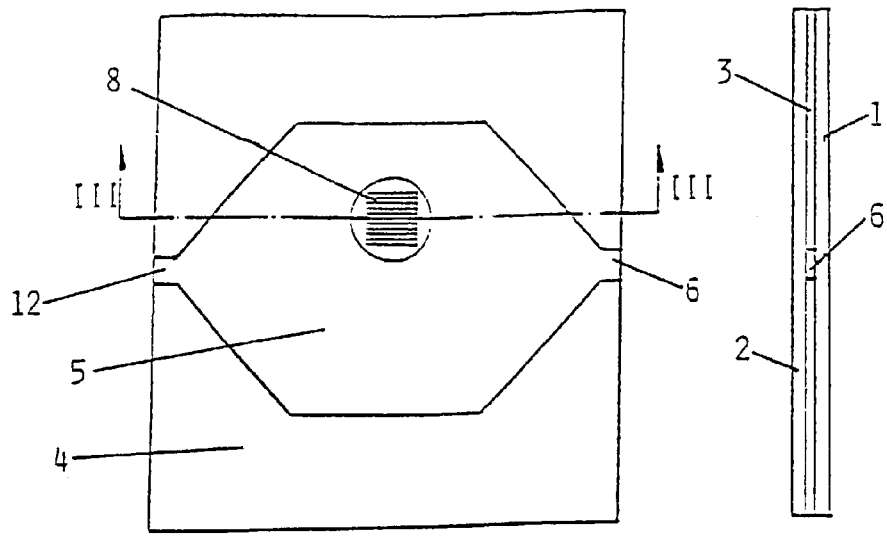
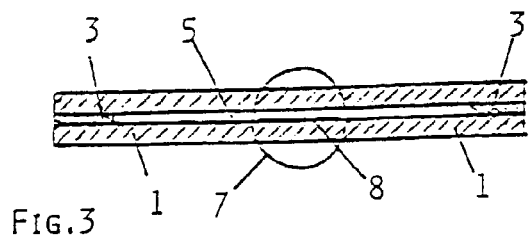
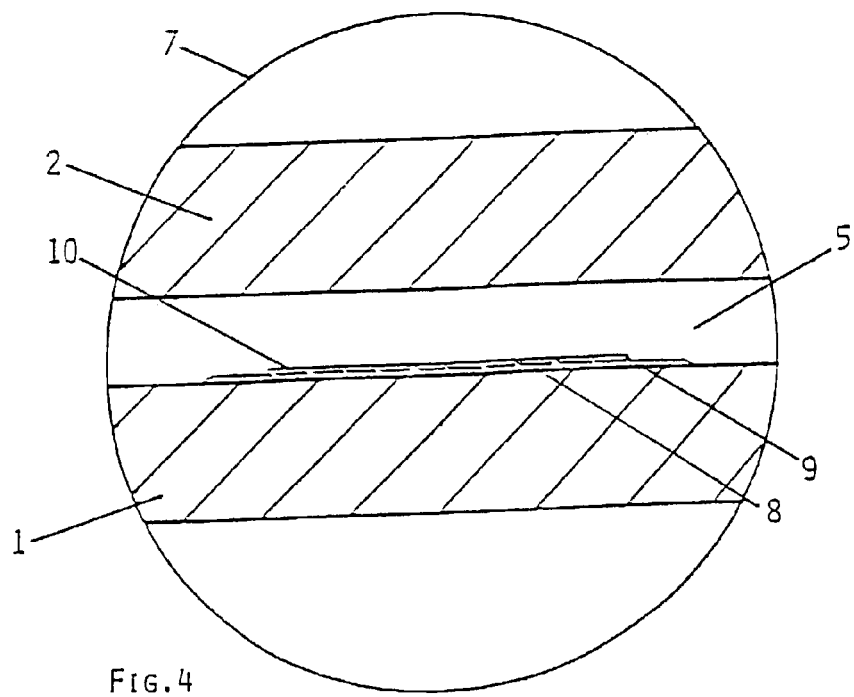

COUNTING CHAMBER PROVIDED WITH A REFERENCE AND METHOD FOR MANUFACTURING A COUNTING CHAMBER PROVIDED WITH A REFERENCE

BACKGROUND OF THE INVENTION

1. Field of the Invention

The invention relates to a counting chamber for optical detection of particles that are present in a fluid, comprising two substantially transparent and substantially parallel plates of material, between which the fluid can be introduced, wherein at least one of said plates includes a visible reference.

2. Description of the Related Art

Such counting chambers can be used for examining blood, urine or sperm and all other fluids.

The term reference is understood to means a visible image, in particular an image which visibly delimits parts of the counting chamber when a person is viewing the counting chamber through a microscope. The particles that are present in the fluid can be quantified in that case by counting or estimating the number of particles that are present in a specific delimited section.

The reference can also be a gauge, which is divided into units of length, so that it is possible to determine the size of the particles that are present in the fluid.

It is important that the reference, or the image, consists of lines which reduce the visibility of the fluid to a minimum degree. It is possible to use extremely thin lines for that purpose, but such lines are difficult to place and, in addition, they do not show up very well at all times.

The object of the invention is to provide a counting chamber including a reference which reduces the degree of visibility in the counting chamber only slightly, and which is nevertheless readily perceptible to the eye.

Another object of the invention is to provide a counting chamber which meets the necessary quality requirements, and which can nevertheless be manufactured at low cost. For hygienic reasons, single use is strongly preferred.

SUMMARY OF THE INVENTION

According to the invention, in order to accomplish that objective, the reference comprises a relief formed on the surface of one of said plates. In practice it has become apparent that a line formed on a surface of at least one of the plates of material in the form of a relief, preferably in the form of a rib projecting from the surface, shows up very well, even if it has a small width, when counting chamber is being viewed through a microscope.

Preferably, the two plates of material are inseparably joined together, for example by means of a glued joint, thus providing a relatively inexpensive, disposable product, that is, a counting chamber for single use.

Preferably, the relief is formed on the inner surface of one of the plates of material, as a result of which the relief extends into the fluid that is present in the counting chamber, as it were.

Such a relief is preferable to a relief that has been formed in a plate of material by, for example, being scratched or etched therein. A thin, straight line is difficult to realise by means of such a method.

In one preferred embodiment, said two plates of material and said relief are transparent, wherein the material of the plates is preferably glass.

In another preferred embodiment, said material is a plastic.

Preferably, said relief consists of a material which extends outwards from the surface of the plate of material, that is, from said plate of material into the space within the counting chamber.

In one preferred embodiment, said reference comprises a grid substantially consisting of lines that intersect each other perpendicularly. In that case the space within the counting chamber appears to be divided into sections upon viewing the contents of the counting chamber, and the number of particles in one section can be counted or estimated.

When the lines, although being readily visible, consist of a transparent material, it is also possible to perceive the particles that are located on a line, which is advantageous when counting said particles.

In another preferred embodiment, said reference comprises a rule provided with a graduation, which makes it possible to determine the size of the particles that are present in said fluid.

Preferably, said relief has been formed in a material different from the material of the plate, for example a synthetic material such as an epoxy resin or an acrylate, which has been applied to the material of the plate. Preferably, said other material has been applied to the plate of material in liquid form and subsequently been compressed by means of a stamp, in which a negative of the relief is present. In that case it is possible to form a relief in the shape of thin, straight ribs, which constitute the reference. After the relief has been formed in this manner, said other material can be cured by exposing it to radiation, for example UV radiation. It is also possible to use infrared radiation.

In another preferred embodiment, said relief comprises grooves that extend into said other material from the surface thereof.

The invention furthermore relates to a method for manufacturing a counting chamber for optical detection of particles that are present in a fluid, wherein two substantially transparent plates of material are joined together in parallel relationship, so that a space is created between said plates, into which said fluid can be introduced, wherein at least one of said plates is previously provided with a visible reference, wherein said reference is formed by forming a relief on the surface of one of said plates.

Preferably, a different material in liquid form is applied to said plate of material, after which it is compressed by means of a stamp, in which a negative of said relief is present. Preferably, said other material is cured by exposing it to UV radiation.

The invention furthermore relates to a method for optical detection of particles that are present in a fluid, wherein said fluid is introduced into a counting chamber comprising two substantially transparent and substantially parallel plates of material, wherein at least one of said plates is provided with a visible reference, wherein said reference comprises a relief that has been formed on the surface of one of said plates.

BRIEF DESCRIPTION OF THE DRAWINGS

In order to explain the invention more fully, an embodiment of a counting chamber will now be explained in more detail with reference to the drawing.

FIG. 1 is a top plan view of a counting chamber;

FIG. 2 is a side elevation of the counting chamber of FIG. 1;

FIG. 3 is a sectional view along line III—III in FIG. 1; and

FIG. 4 is a larger-scale detail of FIG. 3.

DETAILED DESCRIPTION OF THE PREFERRED EMBODIMENTS

The figures show the embodiment only schematically, and for the sake of clarity the dimensions are not shown in their actual proportions in all cases.

FIGS. 1 and 2 show in elevation the counting chamber consisting of two glass plates 1, 2, which are joined by film of glue 3. Said film of glue 3 does not cover the entire area between the glass plates 1, 2, but only the area 4 in FIG. 1, which surrounds an area that forms chamber 5.

Film of glue 3 has a specific thickness, in order to space the glass plates 1, 2 a specific, constant distance apart. Said specific thickness of the film of glue 3 can be achieved by putting spherical particles into the glue, for example glass spheres having a diameter equal to the desired distance between glass plates 1, 2.

Chamber 5 is enclosed by the two glass plates 1, 2 and the film of glue 3, therefore. It is possible to gain access to chamber 5 from the outside via openings 6, 12. Chamber 5 can be filled through one of said openings 6, 12 with a fluid which contains particles that need to be quantified or classified. The other opening 12, 6 thereby functions to vent chamber 5.

FIG. 3 is a sectional view of the counting chamber, and FIG. 4 shows the encircled part 7 of FIG. 3 on a larger scale, so that the reference 8 that is present on lower glass plate 1 is visible.

Reference 8 consists of a film of epoxy resin that has been applied to lower glass plate 1, in which a relief has been formed. In the illustrated embodiment, said relief consists of two groups of eleven mutually parallel ribs each, which extend perpendicularly to each other.

FIG. 4 shows one of said groups of ribs 9 in sectional view. A rib 10 extending perpendicularly thereto is shown in elevation. The circumference of the film of epoxy resin is substantially circular, as is shown in FIG. 1.

Said two groups of eleven ribs 9, 10 each form a grid comprising a hundred square sections, as is shown in FIG. 1. Also other patterns comprising more or fewer ribs are possible, wherein the angle that ribs include between themselves may also be an angle other than a straight one.

The spacing between the two glass plates 1, 2 and the thickness of reference 8 must be selected so that reference 8 and the upper glass plate 2 are spaced a desired distance apart. After all, said spacing determines the amount of fluid that is present within a grid section when chamber 5 is being viewed through a microscope. The number of particles that are present in said amount can be counted or estimated thereby.

In FIG. 1, reference 8 is shown unproportionally large. The spacing between the ribs of the grid is, for example, 0.001–1 mm. The spacing between the glass plates 1, 2 is, for example, 0.1 mm.

Reference 8 may also comprise a rule or other gauge provided with a graduation, whether or not in combination with the grid.

Reference 8 has been formed on glass plate 1 by compressing a drop of a liquid epoxy resin on glass plate 1 by means of a stamp, in which a negative of the relief is present. The curing process of the epoxy resin can be accelerated by exposing it to UV radiation, which can take place through glass plate 1.

In order to make it easier to detach of the stamp, a suitable substance can be applied to the surface thereof, which is done each time before the stamp comes into contact with the epoxy resin or other material.

The illustrated embodiment is merely an example of a counting chamber, also other embodiments are possible.

What is claimed is:

1. A counting chamber for optical detection of particles that are present in a fluid, comprising two substantially transparent and substantially parallel plates of a first material, between which the fluid can be introduced,
   wherein at least one of said plates includes a visible reference comprising a relief formed on a surface of said at least one of said plates in a second material different from said first material of said at least one of said plates, which second material has been applied to said at least one of said plates, wherein said second material is a curable synthetic material.

2. The counting chamber according to claim 1, wherein said two plates are inseparably joined together.

3. The counting chamber according to claim 2, wherein said two plates are inseparably joined together by a glued joint.

4. The counting chamber according to claim 1, wherein said relief is formed on an inner surface of said at least one of said plates.

5. The counting chamber according to claim 1, wherein said first material is glass.

6. The counting chamber according to claim 1, wherein said first material is a plastic.

7. The counting chamber according to claim 1, wherein said relief consists of a material which extends outwards from said surface of said at least one of said plates.

8. The counting chamber according to claim 1, wherein said reference comprises a grid substantially consisting of lines that intersect each other perpendicularly.

9. The counting chamber according to claim 1, wherein said reference comprises a graduation.

10. The counting chamber according to claim 9, wherein said graduation is a rule.

11. The counting chamber according to claim 1, wherein said second material is an epoxy resin or an acrylate.

12. The counting chamber according to claim 1, wherein said second material has been applied to said at least one of said plates in liquid form and subsequently been compressed by means of a stamp, in which a negative of said relief is present.

13. The counting chamber according to claim 12, wherein said second material is cured by exposing said second material to radiation.

14. The counting chamber according to claim 13, wherein said radiation is UV radiation.

15. The counting chamber according to claim 1, wherein said relief comprises grooves that extend into said second material from a surface thereof.

16. A method for optical detection of particles that are present in a fluid, comprising the step of introducing said fluid into a counting chamber comprising two substantially transparent and substantially parallel plates of material, wherein at least one of said plates is provided with a visible reference comprising a relief that has been formed on a surface of said at least one of said plates in a material different from the material of said at least one of said plates, which has been applied to said at least one of said plates, wherein said different material is a curable synthetic material.

* * * * *

UNITED STATES PATENT AND TRADEMARK OFFICE
CERTIFICATE OF CORRECTION

PATENT NO. : 7,016,033 B2
APPLICATION NO. : 10/182367
DATED : March 21, 2006
INVENTOR(S) : De Kock et al.

It is certified that error appears in the above-identified patent and that said Letters Patent is hereby corrected as shown below:

<u>Column 1,</u> Lines 14-15, after "visible reference", insert the following text -- comprising a relief formed on the surface of one of said plates in a material different from the material of the plate, which material has been applied to said plate. --

<u>Column 1,</u> delete the paragraph on Lines 17-18, and replace it with the following paragraph:
    -- Such a counting chamber is described in US 3,146,103, and can be used for examining blood, urine or sperm and all other fluids. The other material of this known counting chamber is comprised of metal particles which are sputtered or printed on a glass plate. In practice it has become apparent that a line formed on a surface of at least one of the plates of material in the form of a relief, preferably in the form of a rib projecting from the surface, shows up very well, even if it has a small width, when the counting chamber is being viewed through a microscope. --

<u>Column 1,</u> Line 19, "understood to means" should read -- understood to mean --

<u>Column 1,</u> Line 43, delete "SUMMARY OF THE INVENTION" and insert that title at Line 34.

<u>Column 1,</u> delete Lines 45-52, and replace them with the following two paragraphs:
    -- According to the invention, in order to accomplish that objective, said other material is a curable synthetic material, for example an epoxy resin or an acrylate. Such a curable material is easier and faster to apply to the plate than metal particles as suggested in US 3,146,103, and therefore the device can be produced in a more cost effective manner. Preferably, said other material has been applied to the plate of material in liquid form and subsequently been compressed by means of a stamp, in which a negative of the relief is present. In that case it is possible to form a relief in the shape of thin, straight ribs, which constitute the reference. After the relief has been formed in this manner, said other material can be cured by exposing it to radiation, for example UV radiation. It is also possible to use infrared radiation.

In another preferred embodiment, said relief comprises grooves that extend into said other material from the surface thereof. --

UNITED STATES PATENT AND TRADEMARK OFFICE
CERTIFICATE OF CORRECTION

PATENT NO. : 7,016,033 B2
APPLICATION NO. : 10/182367
DATED : March 21, 2006
INVENTOR(S) : De Kock et al.

It is certified that error appears in the above-identified patent and that said Letters Patent is hereby corrected as shown below:

Column 2, Lines 1-2, "material is a plastic." should read -- material of the plates is a plastic. --

Column 2, Lines 21-35, delete the paragraph beginning "Preferably said relief has been formed...." and the next paragraph beginning, "In another preferred embodiment, said relief...."

Column 2, Line 44, after "one of said plates.", add the following text -- , and wherein a different material in liquid form is applied to said plate of material, after which it is compressed by means of a stamp, in which a negative of said relief is present. Preferably, said other material is cured by exposing it to UV radiation. --

Column 2, delete the paragraph from Lines 45-49 beginning "Preferably, a different material"

Column 2, Line 56, after "one of said plates.", add the following text -- , and wherein said relief has been formed in a curable synthetic material different from the material of the plate, which has been applied to said plate of material. --

Signed and Sealed this

Twenty-second Day of August, 2006

JON W. DUDAS
*Director of the United States Patent and Trademark Office*